United States Patent
Gabizon et al.

(10) Patent No.: US 12,171,746 B2
(45) Date of Patent: Dec. 24, 2024

(54) LIPOSOME COMPOSITION COMPRISING LIPOSOMAL PRODRUG OF MITOMYCIN C AND METHOD OF MANUFACTURE

(71) Applicants: LIPOMEDIX PHARMACEUTICALS LTD., Jerusalem (IL); SHAARE ZEDEK SCIENTIFIC LTD., Jerusalem (IL)

(72) Inventors: Alberto Gabizon, Jerusalem (IL); Patricia Ohana, Jerusalem (IL); Hilary Shmeeda, Givat Zev (IL)

(73) Assignees: Lipomedix Pharmaceuticals Ltd., Jerusalem (IL); Sharre Zedek Scientific Ltd., Jerusalem (IL)

( * ) Notice: Subject to any disclaimer, the term of this patent is extended or adjusted under 35 U.S.C. 154(b) by 721 days.

(21) Appl. No.: 17/421,959

(22) PCT Filed: Jan. 11, 2020

(86) PCT No.: PCT/IB2020/050205
§ 371 (c)(1),
(2) Date: Jul. 9, 2021

(87) PCT Pub. No.: WO2020/144657
PCT Pub. Date: Jul. 16, 2020

(65) Prior Publication Data
US 2022/0087975 A1    Mar. 24, 2022

Related U.S. Application Data

(60) Provisional application No. 62/791,718, filed on Jan. 11, 2019.

(51) Int. Cl.
| | |
|---|---|
| A61K 31/407 | (2006.01) |
| A61K 9/127 | (2006.01) |
| A61K 9/16 | (2006.01) |
| A61K 47/24 | (2006.01) |
| A61P 35/00 | (2006.01) |

(52) U.S. Cl.
CPC ......... *A61K 31/407* (2013.01); *A61K 9/127* (2013.01); *A61K 9/1617* (2013.01); *A61K 47/24* (2013.01); *A61P 35/00* (2018.01)

(58) Field of Classification Search
None
See application file for complete search history.

(56) References Cited

U.S. PATENT DOCUMENTS

| | | | |
|---|---|---|---|
| 4,808,614 A | 2/1989 | Hertel | |
| 5,464,826 A | 11/1995 | Grindey et al. | |
| 5,472,949 A | 12/1995 | Arasaki et al. | |
| 6,365,179 B1 | 4/2002 | Zalipsky et al. | |
| 6,984,396 B2 | 1/2006 | Zalipsky et al. | |
| 7,303,760 B2 | 12/2007 | Zalipsky et al. | |
| 9,937,261 B2 | 4/2018 | Gabizon et al. | |
| 10,080,807 B2 | 9/2018 | Gabizon et al. | |
| 10,617,672 B2 | 4/2020 | Gabizon et al. | |

FOREIGN PATENT DOCUMENTS

| | | |
|---|---|---|
| CN | 102935068 A | 2/2013 |
| JP | 2018-530623 A | 10/2018 |
| WO | WO 2016/149516 A1 | 9/2016 |
| WO | WO 2017/066667 A1 | 4/2017 |
| WO | WO 2020/144657 | 7/2020 |

OTHER PUBLICATIONS

Xiaohui Wei, Yogita Patil, Patricia Ohana, Yasmine Amitay, Hilary Shmeeda, Alberto Gabizon, and Yechezkel Barenholz Characterization of Pegylated Liposomal Mitomycin C Lipid-Based Prodrug (Promitil) by High Sensitivity Differential Scanning DOI: 10.1021/acs.molpharmaceut.6b00865 (Year: 2017).*
Alberto Gabizon, Yasmine Amitay, Dina Tzemach, Jenny Gorin, Hilary Shmeeda, Samuel Zalipsky Therapeutic efficacy of a lipid-based prodrug of mitomycin C in pegylated liposomes: Studies with human gastro-entero-pancreatic DOI: 10.1016/j.jconrel.2011.11.019 (Year: 2012).*
Xiaohui Wei et al: Characterization of Pegylated Liposomal Mitomycin C Lipid-Based Prodrug (Promitil) by High Sensitivity Differential Scanning Calorimetry and Cryogenic Transmission Electron Microscopy doi.org/10.1021/acs.molpharmaceut.6b00865 (Year: 2017).*
Alberto Gabizon et al: Therapeutic efficacy of a lipid-based prodrug of mitomycin C in pegylated liposomes: Studies with human gastro-entero-pancreatic ectopic tumor models:A. Gabizon et al. / Journal of Controlled Release 160 (2012) 245-253 (Year: 2012).*
Gabizon et al., "Reduced toxicity and superior therapeutic activity of a mitomycin C lipid-based prodrug incorporated in pegylated liposomes", Clin. Cancer Res., vol. 12, No. 6, pp. 1913-1920 (2006).
International Search Report from International Patent Application No. PCT/IB2020/050205, 5 pages, mailed May 8, 2020.
Sandstrom et al., "Structure of mixed micelles formed in PEG-lipid/lipid dispersions". Langmuir, vol. 23, No. 8, pp. 4192-4198 (2007).

(Continued)

*Primary Examiner* — Robert A Wax
*Assistant Examiner* — Andre Mach
(74) *Attorney, Agent, or Firm* — McDermott Will & Emery LLP; Judy M. Mohr

(57) ABSTRACT

A liposome composition comprising a lipophilic prodrug of mitomycin C having an improved pharmacokinetic profile is described. A method for preparing the composition with a solvent system comprised of ethanol and tertiary butanol mixed at an adequate ratio is also described. In an embodiment, the liposome composition is a population of lipid nanoparticles and a pharmaceutically acceptable vehicle, wherein the population of lipid nanoparticles is comprised of a first fraction of spherical liposomes and a second fraction of rod-shaped lipid nanoparticles, where the second fraction is less than about 15% of the population of lipid nanoparticles.

19 Claims, 6 Drawing Sheets

(56) References Cited

OTHER PUBLICATIONS

Wei et al., "Characterization of Pegylated Liposomal Mitomycin C Lipid-Based Prodrug (Promitil) by High Sensitivity Differential Scanning Calorimetry and Cryogenic Transmission Electron Microscopy", Mol. Pharm., vol. 14, No. 12, pp. 4339-4345 (2017).

Zhang et al., "The effect of DSPE-PEG 2000, cholesterol and drug incorporated in bilayer on the formation of discoidal micelles", European J. Pharm. Sci., vol. 125, pp. 74-85 (2018).

Patil et al., "Targeting of pegylated liposomal mitomycin-C prodrug to he folate receptor of cancer cells: Intracellular activation and enhanced cytotoxicity", Journal of Controlled Release, vol. 225, pp. 87-95 (2016).

Patil et al., "Targeting of folate-conjugated liposomes with co-entrapped drugs to prostate cancer cells via prostate-specific membrane antigen (PSMA)", Nanomedicine, vol. 14, No. 2, pp. 1407-1416 (2018).

Amitay et al., "Pharmacologic Studies of a Prodrug of Mitomycin C in Pegylated Liposomes (Promitil(@)): High Stability in Plasma and Rapid Thiolytic Prodrug Activation in Tissues", Pharm. Res., vol. 33, No. 3, pp. 686-700 (Mar. 2016).

\* cited by examiner

90%EtOH-10% tButOH

100% EtOH

75% EtOH-25% tButOH

EtOH 50%-tButOH50%

LIPOSOME COMPOSITION COMPRISING LIPOSOMAL PRODRUG OF MITOMYCIN C AND METHOD OF MANUFACTURE

CROSS-REFERENCE TO RELATED APPLICATIONS

This application is a U.S. National Stage Application under 35 U.S.C. § 371 which claims the benefit of priority to International Patent Application No. PCT/IB2020/050205, filed Jan. 11, 2020, which claims the benefit of priority to Provisional Patent Application No. 62/791,718 filed Jan. 11, 2019, each of which is hereby incorporated by reference in its entirety.

TECHNICAL FIELD

The subject matter described herein relates to a liposome composition comprising a lipophilic prodrug of mitomycin C, preparation thereof, and use thereof.

BACKGROUND

Cancer is a leading cause of death in the United States and affects people worldwide. Surgery, radiation and chemotherapy are the most widely used therapeutic modalities. Chemotherapy agents create conditions within the cell that limit cell growth and replication, and cancer chemotherapy has advanced dramatically in recent years. Chemotherapy agents typically affect both neoplastic and rapidly proliferating cells of normal tissue such as bone marrow, hair follicles and intestinal epithelium. Anorexia, nausea, vomiting, diarrhea, suppression of bone marrow function and hair loss are some of the negative effects commonly associated with chemotherapy. Development of a chemotherapy agent that provide effective antitumor therapy with minimal toxicity would be advantageous.

A liposome formulation comprising 5 mole percent of the liposomal prodrug conjugate of mitomycin C and preparation thereof were disclosed in U.S. Pat. No. 6,365,179. To reduce the amount of lipids excipient for delivering a sufficient dose of the mitomycin C prodrug, a liposome formulation comprising more than 5 mole percent, such as about 10 mole percent, of the liposomal mitomycin C prodrug is desired. Ethanol, the solvent used to dissolve the liposome components comprising 5 mole percent of the mitomycin C prodrug for the preparation of liposome formulations, was found to be unable to dissolve properly the liposome components comprising about 10 mole percent of the mitomycin C prodrug. Without tertiary butanol, solubilization of the mitomycin C prodrug was a difficult and incomplete process resulting in precipitates, and vesicle size growth. A solvent mixture of ethanol/tertiary-butanol (50/50, v/v) can dissolve the liposome components comprising about 10 mole percent of the mitomycin C prodrug.

The liposome formulation prepared by a process comprising dissolving the liposome components in the solvent mixture of ethanol/tertiary-butanol (50/50, v/v) suffers drawbacks such as formation of rod-like particles (collapsed or discoidal liposomes), and fast plasma clearance.

This application discloses a new method of preparing a liposome formulation comprising a lipophilic prodrug conjugate of mitomycin C. The liposome formulation as disclosed herein is essentially free of rod-shaped lipid nanoparticles and provides a blood concentration of mitomycin C prodrug and a blood circulation time of mitomycin C prodrug that are improved, when compared with prior liposome compositions comprising a lipophilic prodrug conjugate of mitomycin C.

BRIEF SUMMARY

The following aspects and embodiments thereof described and illustrated below are meant to be exemplary and illustrative, not limiting in scope.

In one aspect, a composition is provided. The composition comprises a population of lipid nanoparticles and a pharmaceutically acceptable vehicle, wherein the population of the lipid nanoparticles is comprised of a first fraction of spherical liposomes and a second fraction of rod-shaped lipid nanoparticles, where the second fraction is less than about 15% of the population of the lipid 1 nanoparticles, wherein the spherical liposomes are comprised of a vesicle-forming lipid, a lipophilic prodrug of mitomycin C, and an optional lipid component.

In one embodiment, the amount of the lipophilic prodrug of mitomycin C is greater than 5% but less than 30% by moles of the total moles of the vesicle-forming lipid, lipophilic prodrug of mitomycin C, and optional lipid component. In some embodiments, the amount of the lipophilic prodrug of mitomycin C is about 8, 9, 10, 11, or 12% by moles of the total moles of the vesicle-forming lipid, lipophilic prodrug of mitomycin C, and optional lipid component.

In one embodiment, the second fraction of rod-shaped lipid nanoparticles is less than about 5% of the population of lipid nanoparticles.

In another embodiment, wherein the second fraction is between about 0.1-5% of the population of the lipid nanoparticles.

In yet another embodiment, the population of lipid nanoparticles is manufactured by a process comprising dissolving the vesicle-forming lipid, lipophilic prodrug of mitomycin C, and optional lipid component in a solvent mixture comprised of ethanol and tertiary butanol in an ethanol/tertiary-butanol ratio (v/v) of between about 2:1 to 20:1. In some embodiments, the ethanol/tertiary-butanol ratio (v/v) is between about 5:1 to 20:1. In some embodiments, the ethanol/tertiary-butanol ratio (v/v) is between about 7:1 to 15:1. In some embodiments, the ethanol/tertiary-butanol ratio (v/v) is about 9:1.

In still another embodiment, the optional lipid component is selected from cholesterol and a conjugate of polyethyleneglycol attached to a lipophilic moiety.

In still yet another embodiment, the liposomal prodrug of mitomycin C of the composition disclosed herein has an W blood circulation half-life in mice of at least about 15 hours.

In still yet another embodiment, the liposomal prodrug of mitomycin C of the composition disclosed herein has a blood circulation half-life in mice after intravenous administration that is substantially the same as or within about 10%, 15%, or 20% shorter than the blood circulation half-life in mice after intravenous administration of a pegylated liposomal doxorubicin composition, such as that known as DOXIL®. In contrast, a liposomal prodrug of mitomycin C of a composition comprising equal to or greater than about 15% of rod-shaped lipid nanoparticles has a blood circulation half-life in mice after intravenous administration that is 25%, 35% or 45% shorter than the blood circulation half-life in mice after intravenous administration of a pegylated liposomal doxorubicin composition, such as that known as DOXIL®.

In one embodiment, about 24 hours after intravenous injection into mice of the composition disclosed herein, the liposomal prodrug of mitomycin C has a concentration in mice plasma that is greater than 20% of Cmax of the liposomal prodrug of mitomycin C in mice plasma after intravenous injection.

In another aspect, a method for the manufacture of lipid nanoparticles is provided. The method comprises dissolving a vesicle-forming lipid, a lipophilic prodrug of mitomycin C, and an optional lipid component in a solvent mixture comprised of ethanol and tertiary butanol in an ethanol/tertiary-butanol ratio (v/v) of between about 2:1 to 20:1 to form a dissolved lipid solution and forming a population of lipid nanoparticles, wherein the population of lipid nanoparticles is comprised of a first fraction of spherical liposomes and a second fraction of rod-shaped lipid nanoparticles, where the second fraction is less than about 15% of the population of lipid nanoparticles.

In one embodiment, forming the population of lipid nanoparticles comprises mixing the dissolved lipid solution with an aqueous buffer to form a suspension, extruding the suspension through filters, and removing the mixture of ethanol and tertiary-butanol. In some embodiments, forming the population of lipid nanoparticles further comprises sterile filtration.

In one embodiment, the amount of the lipophilic prodrug of mitomycin C is greater than 5% but less than 30% by moles of the total moles of the vesicle-forming lipid, lipophilic prodrug of mitomycin C, and optional lipid component. In some embodiments, the amount of the lipophilic prodrug of mitomycin C is about 8, 9, 10, 11, or 12% by moles of the total moles of the vesicle-forming lipid, lipophilic prodrug of mitomycin C, and optional lipid component.

In still another embodiment, the optional lipid component is selected from cholesterol and a conjugate of polyethyleneglycol attached to a lipophilic moiety.

In one embodiment, the ethanol/tertiary-butanol ratio (v/v) is between about 5:1 to 20:1 or is between about 7:1 to 15:1. In one embodiment, the ethanol/tertiary-butanol ratio (v/v) is about 9:1.

In one embodiment, the second fraction is less than about 5% of the population of lipid nanoparticles.

In one embodiment, the second fraction is between about 0.1-5% of the population of lipid nanoparticles.

In yet another aspect, a population of lipid nanoparticle prepared by a process is provided, wherein the process comprises dissolving a vesicle-forming lipid, a lipophilic prodrug of mitomycin C, and an optional lipid component in a solvent mixture comprised of ethanol and tertiary butanol in an ethanol/tertiary-butanol ratio of between about 2:1 to 20:1 to form a dissolved lipid solution; and mixing the dissolved lipid solution with an aqueous buffer to form a population of lipid nanoparticles, wherein the population of lipid nanoparticles is comprised of a first fraction of spherical liposomes and a second fraction of rod-shaped lipid nanoparticles, where the second fraction is less than about 15% of the population of lipid nanoparticles.

In yet another aspect, a method of treating cancer is provided. The method comprises providing a liposome composition comprised of a population of lipid nanoparticles suspended in a pharmaceutically acceptable vehicle, the population of lipid nanoparticles comprised of a first fraction of spherical liposomes and a second fraction of rod-shaped lipid nanoparticles, where the second fraction is less than about 15% of the population of lipid nanoparticles; and administering the liposomes to a patient in need thereof in an amount that provides a therapeutically-effective amount of mitomycin C prodrug for the treatment of cancer.

In addition to the exemplary aspects and embodiments described above, further aspects and embodiments will become apparent by reference to the drawings and by study of the following descriptions.

Additional embodiments of each of the aspects will be apparent from the following description, drawings, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment of the present invention. Additional aspects and advantages of the present invention are set forth in the following description and claims, particularly when considered in conjunction with the accompanying examples and drawings.

DETAILED DESCRIPTION

I. Definitions

Figure 1A:
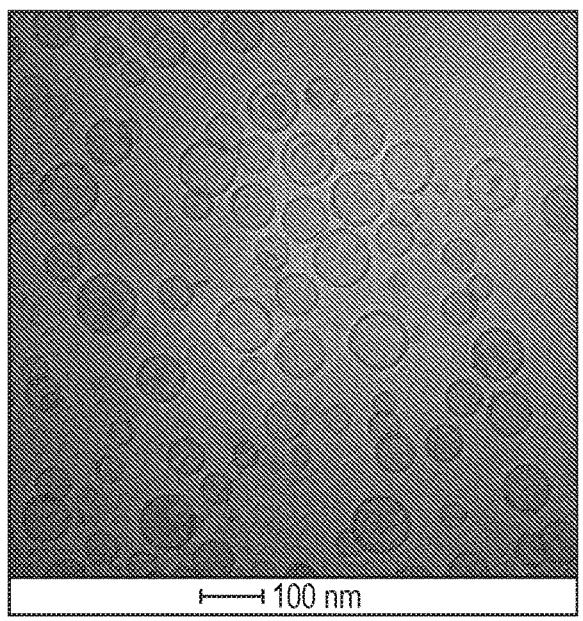
FIGS. 1A-1D are cryotransmission electron microscopy (cryo-TEM) images of liposomes prepared by a process comprising dissolving liposome components in a solvent with ratio (v/v) of ethanol/tertiary-butanol at 50:50 (FIG. 1D), 75:25 (FIG. 1C), 90:1, (FIG. 1A) and 100:0 (FIG. 1B), respectively.

Various aspects now will be described more fully hereinafter. Such aspects may, however, be embodied in many different forms and should not be construed as limited to the embodiments set forth herein; rather, these embodiments are provided so that this disclosure will be thorough and complete, and will fully convey its scope to those skilled in the art.

"Administering" or "administration" as used herein means the introduction of a foreign molecule into a cell or host. The term is intended to be synonymous with the term "delivery" or "delivering". Suitable routes of administration, without limitation, are intravenous, intra-arterial, intramuscular, subcutaneous, intraperitoneal, intrapleural, intrathecal, intravesical or intratumoral, intrasynovial, infusion, sublingual, transdermal, oral, or topical.

As used herein, Cmax refers to the maximum concentration that a drug (such as the liposomal mitomycin C prodrug) achieves in the plasma of a subject (such as an animal for example mice or such as a human) after the drug has been administered to the subject. It is a standard measurement used in the study of pharmacokinetics.

As used herein, the phrase "chemotherapeutic agent" is synonymous with and "antineoplastic agent" or "antiproliferative agent" and refers to compounds that prevent cancer, or hyperproliferative cells, from multiplying. Generally, antineoplastic agents may prevent cancer cells from multiplying by: (1) interfering with the cell's ability to replicate DNA and (2) inducing cell death and/or apoptosis in the cancer cells.

An amount of liposomal-mitomycin C prodrug that yields a therapeutically-effective amount of mitomycin C after administration is an amount of mitomycin C prodrug that is effective to ameliorate or minimize the clinical impairment or symptoms of the neoplasia, in either a single or multiple doses.

"Intravenous blood circulation half-life" or "IV blood circulation half-life" refers to blood circulation half-life of the referenced drug (such as liposomal mitomycin C prodrug) administered via intravenous injection to referenced subject (such as nice).

As used herein, a "neoplasm" or "neoplasia" means a proliferative disease characterized by the abnormal proliferation of cells. Typically, neoplasia is associated with cancer and tumor formation. As used herein a "solid tumor" is one that occurs in an organ, such as the breast or the colon.

The term "patient" refers to an individual afflicted with a disease characterized by neoplasia. In particular, a patient (i.e., a host) is an animal (i.e., mammal) or human.

As used herein, "pharmaceutical formulations" include formulations for human and veterinary use with no significant adverse effect. "Pharmaceutically acceptable carrier" as used herein refers to a composition or formulation that allows for the effective distribution of the agents of the instant invention in the physical location most suitable for their desired activity and "pharmaceutically acceptable carrier" refers to a buffer, stabilizer or other material well known to those skilled in the art. Such materials should be non-toxic and should not interfere with the efficacy of the active ingredient. The precise nature of the carrier or other material may depend on the route of administration.

As used herein, "prodrug" means a compound that is a drug precursor which, following administration to a subject, releases the drug in vivo via some chemical or physiological process such that the prodrug is converted into a product that is toxic to cells of a neoplasm.

Reference to a "therapeutically effective amount," intends an amount of a compound sufficient to show benefit to the individual. This amount prevents, alleviates, abates, or otherwise reduces the severity of a symptom associated with neoplasia in a patient, such as a reduction in tumor mass or volume or a slowing of tumor growth rate.

The terms "treat," "treatment" and "therapeutic effect" as used herein refer to reducing or stopping a cell proliferation rate (e.g., slowing or halting tumor growth) or reducing the number of proliferating cancer cells.

The percentage of second fraction of rod-shaped lipid nanoparticles relative to the population of lipid nanoparticles refers to percentage by numbers of the rod-shaped lipid nanoparticles relative to numbers of lipid nanoparticles in the population.

Where a range of values is provided, it is intended that each intervening value between the upper and lower limit of that range and any other stated or intervening value in that stated range is encompassed within the disclosure. For example, if a range of 1 μm to 8 μm is stated, it is intended that 2 μm, 3 μm, 4 μm, 5 μm, 6 μm, and 7 μm are also explicitly disclosed, as well as the range of values greater than or equal to 1 μm and the range of values less than or equal to 8 μm.

The singular forms "a," "an," and "the" include plural referents unless the context clearly dictates otherwise. Thus, for example, reference to a "liposome" includes a single liposome as well as two or more of the same or different liposomes, reference to an "excipient" includes a single excipient as well as two or more of the same or different excipients, and the like.

The term "about," particularly in reference to a given quantity, is meant to encompass deviations of plus or minus 5%, 10%, 15% or 20%.

II. Liposome Compositions

In one aspect, a composition is provided. The composition comprises a population of lipid nanoparticles and a pharmaceutically acceptable vehicle, wherein the population of lipid nanoparticles is comprised of a first fraction of spherical liposomes and a second fraction of rod-shaped lipid nanoparticles, where the second fraction is less than about 15% of the population of lipid nanoparticles, and wherein the spherical liposomes are comprised of a vesicle-forming lipid, a lipophilic prodrug of mitomycin C, and an optional lipid component.

In one embodiment, the amount of the lipophilic prodrug of mitomycin C is greater than 5% but less than 30%, such as greater than greater than 5% but less than 20%, by moles of the total moles of the vesicle-forming lipid, lipophilic prodrug of mitomycin C, and optional lipid component. In some embodiments, the amount of the lipophilic prodrug of mitomycin C is about 8, 9, 10, 11, or 12%, such as 10% by moles of the total moles of the vesicle-forming lipid, lipophilic prodrug of mitomycin C, and optional lipid component.

In one embodiment, the second fraction is less than about 5% of the population of lipid nanoparticles.

In one embodiment, the second fraction is between about 0.1-5% of the population of lipid nanoparticles.

In one embodiment, the population of lipid nanoparticles is manufactured by a process comprising dissolving the vesicle-forming lipid, lipophilic prodrug of mitomycin C, and optional lipid component in a solvent mixture comprised of ethanol and tertiary butanol in an ethanol/tertiary-butanol ratio (v/v) of between about 2:1 to 20:1. In some embodiments, the ethanol/tertiary-butanol ratio (v/v) is between about 5:1 to 20:1. In some embodiments, the ethanol/ tertiary-butanol ratio (v/v) is between about 7:1 to 15:1. In some embodiments, the ethanol/tertiary-butanol ratio (v/v) is about 9:1.

In one embodiment, the liposomal prodrug of mitomycin C of the composition disclosed herein has an IV blood circulation half-life in mice of at least about 15 hours.

In one embodiment, comparing to liposomal prodrug of mitomycin C of a composition comprising equal to or greater than about 15% of rod-shaped lipid nanoparticles, the liposomal prodrug of mitomycin C of the composition disclosed herein has an IV blood circulation half-life in mice that is closer in value to the IV blood circulation half-life in mice of pegylated liposomal doxorubicin.

In one embodiment, the liposomal prodrug of mitomycin C of the composition disclosed herein has a blood circulation half-life in mice after intravenous administration that is substantially the same as or within about 10%, 15%, or 20% shorter than the blood circulation half-life in mice after intravenous administration of a pegylated liposomal doxorubicin composition. In contrast, a liposomal prodrug of mitomycin C of a composition comprising equal to or greater than about 15% of rod-shaped lipid nanoparticles has a blood circulation half-life in mice after intravenous administration that is 25%, 35% or 45% shorter than the blood circulation half-life in mice after intravenous administration of a pegylated liposomal doxorubicin composition, such as that known as DOXIL®.

In one embodiment, about 24 hours after intravenous injection into mice of the composition disclosed herein, the liposomal prodrug of mitomycin C has a concentration in mice plasma that is greater than 20% of Cmax of the liposomal prodrug of mitomycin C in mice plasma after intravenous injection.

A. Liposomal Mitomycin C Prodrug

The liposomal prodrug conjugate of mitomycin C or liposomal-mitomycin C prodrug conjugate provided for use in the compositions and methods described herein refers to the prodrug conjugate of mitomycin C incorporated into a liposome delivery platform, and in one embodiment, the prodrug conjugate of mitomycin C is comprised of mitomycin C releasably attached to a lipophilic or hydrophobic moiety, and generally is of the form:

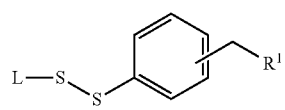

wherein L is a hydrophobic moiety, $R^1$ represents a mitomycin C residue covalently attached to the dithiobenzyl moiety. Orientation of the $CH_2R^1$ group is selected from the ortho position and the para position. Synthesis of the conjugate is described in U.S. Pat. Nos. 6,365,179; 6,984,396; and 7,303,760, each of which is incorporated by reference herein.

The hydrophobic moiety, L, is typically a lipid such as a diacylglycerol, a sterol, a phospholipid, derivatives of these lipids, other naturally-occurring lipids and their synthetic analogs. The hydrophobic moiety is suitable for incorporation into a liposomal bilayer, to anchor the mitomycin C conjugate to a liposomal delivery vehicle.

In one embodiment, the lipophilic prodrug conjugate of mitomycin C has the following structure:

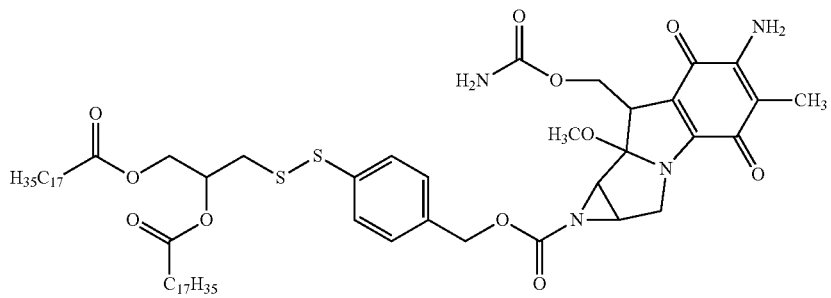

Para-diacyldiglyceroldithiobenzyl-mitomycin C (para-distearoyl-DTB-mitomycin C)

The liposomal-mitomycin C prodrug conjugate upon exposure to reducing conditions, i.e., a reducing agent such as cysteine or glutathione, decomposes to yield mitomycin C. That is, thiolytic cleavage of the conjugate yields mitomycin C and non-toxic by products of the hydrophobic moiety and the dithiobenzyl moiety. As can be appreciated, the prodrug conjugate can be readily incorporated into liposomes for administration in vivo to a subject. The prodrug conjugate is not toxic, and after administration and upon exposure to endogenous reducing agents or exposure to an exogenous reducing agent, the conjugate decomposes to yield mitomycin C in its native state and with biological activity.

B. Liposomes

Liposomes are closed lipid vesicles used for a variety of therapeutic purposes, and in particular, for carrying therapeutic agents to a target region or cell by systemic administration of liposomes. In particular, liposomes having a surface coating of hydrophilic polymer chains, such as polyethylene glycol (PEG), are desirable as drug carries as these liposomes offer an extended blood circulation lifetime over liposomes lacking the polymer coating. The polymer acts as a barrier to blood proteins thereby preventing binding of the protein and recognition of the liposomes for uptake and removal by macrophages and other cells of the reticuloendothelial system. Liposomes in the ultra-filterable size range (less than 200 nm diameter) are considered and often referred to as lipidic lipid nanoparticles or simply lipid nanoparticles.

Liposomes within the scope of the present disclosure can include a conjugate in combination with a lipid, which in one embodiment is a vesicle-forming lipid, and, optionally, at least one lipid components. The at least one optional lipid component as used in this disclosure can be selected from cholesterol and lipid bilayer stabilizing lipid, for example, a conjugate of polyethyleneglycol attached to a lipophilic moiety, such as methoxy-polyethylene glycol-distearoyl phosphatidylethanolamine (mPEG-DSPE).

"Vesicle-forming lipids" are lipids that spontaneously form bilayer vesicles in water. The vesicle-forming lipids preferably have two hydrocarbon chains, typically acyl chains, and a polar head group. There are a variety of synthetic vesicle-forming lipids and naturally-occurring vesicle-forming lipids known in the art where the two hydrocarbon chains are typically from about 12 to about 24 carbon atoms in length, and have varying degrees of unsaturation. Examples include the phospholipids, such as phosphatidylcholine (PC), phosphatidylethanolamine (PE), phosphatidic acid (PA), phosphatidylinositol (PI), and sphingomyelin (SM). A preferred lipid for use in the present invention is hydrogenated soy phosphatidylcholine (HSPC). Another preferred family of lipids are diacylglycerols. These lipids can be obtained commercially or prepared according to published methods.

The vesicle-forming lipid may be selected to achieve a degree of fluidity or rigidity, to control the stability of the liposome in serum, and to control the rate of release of an entrapped agent in the liposome. Liposomes having a more rigid lipid bilayer, or a liquid crystalline bilayer, can be prepared by incorporation of a relatively rigid lipid, e.g., a lipid having a relatively high phase transition temperature, e.g., up to about 65° C. Rigid lipids, i.e., saturated, contribute to greater membrane rigidity in the lipid bilayer. Other lipid components, such as cholesterol, are also known to contribute to membrane rigidity in lipid bilayer structures.

Lipid fluidity is achieved by incorporation of a relatively fluid lipid, typically one having a lipid phase with a relatively low liquid to liquid-crystalline phase transition temperature, e.g., at or below room temperature (about 20-25° C.).

The liposome can also include other lipid components that can be incorporated into lipid bilayers, such as sterols. These other lipid components typically have a hydrophobic moiety in contact with the interior, hydrophobic region of the bilayer membrane, and a polar head group moiety oriented toward the exterior, polar surface of the membrane.

Another lipid component in the liposomes can be a vesicle-forming lipid derivatized with a hydrophilic polymer. In this lipid component, a derivatized lipid results in formation of a surface coating of hydrophilic polymer chains on both the inner and outer lipid bilayer surfaces. Typically, between about 1-20 mole percent of the derivatized lipid is included in the lipid composition.

Hydrophilic polymers suitable for derivatization with a vesicle-forming lipid include polyvinylpyrrolidone, polyvinylmethylether, polymethyloxazoline, polyethyloxazoline, polyhydroxypropyloxazoline, polyhydroxypropylmethacrylamide, polymethacrylamide, polydimethylacrylamide, polyhydroxypropylmethacrylate, polyhydroxyethylacrylate, hydroxymethylcellulose, hydroxyethylcellulose, polyethyleneglycol, and polyaspartamide. The polymers may be employed as homopolymers or as block or random copolymers.

A preferred hydrophilic polymer chain is polyethyleneglycol (PEG), preferably as a PEG chain having a molecular weight between about 500 to about 10,000 Daltons, preferably between about 1,000 to about 5,000 Daltons. Methoxy or ethoxy-capped analogues of PEG are also preferred hydrophilic polymers. These polymers are commercially available in a variety of polymer sizes, e.g., from about 12 to about 220,000 Daltons.

Liposomes can include typically between about 1 and about 30 mole percent of the lipid-mitomycin C prodrug conjugate, preferably between about 5 and about 30 mole percent, more preferably between about 5 and about 20 mole percent, such as greater than 5 mole percent but less than 30 mole percent, greater than 5 mole percent but less than 20 mole percent, or about 8, 9, 10, 11, and 12 mole percent.

In one embodiment, the vesicle-forming liposome can be HSPC. In one embodiment, the optional lipid component is selected from mPEG2000-DSPE and cholesterol.

In one embodiment, the liposomes can include HSCP, cholesterol, mPEG2000-DSPE, and para-distearoyl-DTB-mitomycin C with HSCP/cholesterol/mPEG2000-DSPE/para-distearoyl-DTB-mitomycin C present at a molar ratio of 55/30/5/10.

C. Methods of Manufacture

The liposome formulation prepared by a process comprising dissolving the liposome components in the solvent mixture of ethanol/tertiary-butanol (50/50, v/v) suffers drawbacks such as fast pharmacokinetic clearance. When reducing the amount of tertiary-butanol in the solvent mixture, the pharmacokinetic clearance rate of the lipophilic mitomycin C prodrug was unexpectedly decreased, and the amount of the rod-shaped liposomes was also reduced.

Hence, a new method for the manufacture of liposomes is provided. The method comprises dissolving a vesicle-forming lipid, a lipophilic prodrug of mitomycin C, and an optional lipid component in a solvent mixture comprised of ethanol and tertiary butanol in an ethanol/tertiary-butanol ratio (v/v) of between about 2:1 to 20:1 to form a dissolved lipid solution and forming a population of lipid nanoparticles, wherein the population of lipid nanoparticles is comprised of a first fraction of spherical liposomes and a second fraction of rod-shaped lipid nanoparticles, where the second fraction is less than about 15% of the population of lipid nanoparticles.

In one embodiment, forming the population of lipid nanoparticles comprises mixing the dissolved lipid solution with an aqueous buffer to form a suspension, extruding the suspension through filters, and removing the mixture of ethanol and tertiary-butanol. In some embodiments, forming the population of lipid nanoparticles further comprises sterile filtration.

In one embodiment, the amount of the lipophilic prodrug of mitomycin C is greater than 5% but less than 30%, such as greater than 5% but less than 20%, by moles of the total moles of the vesicle-forming lipid, lipophilic prodrug of mitomycin C, and optional lipid component. In some embodiments, the amount of the lipophilic prodrug of mitomycin C is about 8, 9, 10, 11, or 12% by moles of the total moles of the vesicle-forming lipid, lipophilic prodrug of mitomycin C, and optional lipid component.

In still another embodiment, the optional lipid component is selected from cholesterol and a conjugate of polyethyleneglycol attached to a lipophilic moiety.

In one embodiment, the ethanol/tertiary-butanol ratio (v/v) is between about 5:1 to 20:1 or is between about 7:1 to 15:1. In one embodiment, the ethanol/tertiary-butanol ratio (v/v) is about 9:1.

In one embodiment, the second fraction is less than about 5% of the population of lipid nanoparticles.

In one embodiment, the second fraction is between about 0.1-5% of the population of lipid nanoparticles In one embodiment, the lipophilic prodrug conjugate of mitomycin C is para-distearoyl-DTB-mitomycin C.

In one embodiment, the vesicle-forming liposome is HSPC.

In one embodiment, the optional lipid component comprises mPEG2000-DSPE.

In one embodiment, the optional lipid component comprises cholesterol and mPEG2000-DSPE.

In one embodiment, the liposomes comprise HSCP, cholesterol, mPEG2000-DSPE, and para-distearoyl-DTB-mitomycin C with HSCP/cholesterol/mPEG2000-DSPE/para-distearoyl-DTB-mitomycin C present at a molar ratio of 55/30/5/10.

Also provided is a population of lipid nanoparticles prepared by a process, comprising dissolving a vesicle-forming lipid, a lipophilic prodrug of mitomycin C, and an optional lipid component in a solvent mixture comprised of ethanol and tertiary butanol in an ethanol/tertiary-butanol ratio of between about 2:1 to 20:1 to form a dissolved lipid solution; and mixing the dissolved lipid solution with an aqueous buffer to form a population of lipid nanoparticles, wherein the population of lipid nanoparticles is comprised of a first fraction of spherical liposomes and a second fraction of rod-shaped lipid nanoparticles, where the second fraction is less than about 15% of the population of lipid nanoparticles.

In one embodiment, the amount of the lipophilic prodrug of mitomycin C is greater than 5% but less than 30%, such as greater than 5% but less than 20%, by moles of the total moles of the vesicle-forming lipid, lipophilic prodrug of mitomycin C, and optional lipid component. In some embodiments, the amount of the lipophilic prodrug of mitomycin C is about 8, 9, 10, 11, or 12% by moles of the total moles of the vesicle-forming lipid, lipophilic prodrug of mitomycin C, and optional lipid component.

In still another embodiment, the optional lipid component is selected from cholesterol and a conjugate of polyethyleneglycol attached to a lipophilic moiety.

In one embodiment, the amount of the lipophilic prodrug of mitomycin C is greater than 5% but less than 30% by moles of the total moles of the lipids. In some embodiments, the amount of the lipophilic prodrug of mitomycin C is about 10% by moles of the total moles of the liposomes In one embodiment, the ethanol/tertiary-butanol ratio (v/v) is between about 5:1 to 20:1 or is between about 7:1 to 15:1. In one embodiment, the ethanol/tertiary-butanol ratio (v/v) is about 9:1.

In one embodiment, the second fraction is less than about 5% of the population of lipid nanoparticles.

In one embodiment, the second fraction is between about 0.1-5% of the population of lipid nanoparticles In one embodiment, the lipophilic prodrug conjugate of mitomycin C is para-distearoyl-DTB-mitomycin C.

In one embodiment, the vesicle-forming liposome is HSPC.

In one embodiment, the optional lipid component comprises mPEG2000-DSPE.

In one embodiment, the optional lipid component comprises cholesterol and mPEG2000-DSPE.

In one embodiment, the liposomes comprises HSCP, cholesterol, mPEG2000-DSPE, and para-distearoyl-DTB-mitomycin C with HSCP/cholesterol/mPEG2000-DSPE/para-distearoyl-DTB-mitomycin C present at a molar ratio of 55/30/5/10.

III. Methods of Treatment

In one aspect, a method of treating cancer is provided. The method comprises providing a liposome composition comprised of a population of lipid nanoparticles suspended in a pharmaceutically acceptable vehicle, the population of lipid nanoparticles comprised of a first fraction of spherical liposomes and a second fraction of rod-shaped lipid nanoparticles, where the second fraction is less than about 15% of the population of lipid nanoparticles; and administering the liposomes to a patient in need thereof in an amount that provides a therapeutically-effective amount of mitomycin C for the treatment of cancer.

In one embodiment, the spherical liposome comprises a vesicle-forming lipid, a lipophilic prodrug of mitomycin C, and an optional lipid component.

In one embodiment, the population of lipid nanoparticles is manufactured by a process comprising dissolving the vesicle-forming lipid, lipophilic prodrug of mitomycin C, and optional lipid component in a solvent mixture comprised of ethanol and tertiary butanol in an ethanol/tertiary-butanol ratio (v/v) of between about 2:1 to 20:1. In some embodiments, the ethanol/tertiary-butanol ratio (v/v) is between about 5:1 to 20:1. In some embodiments, the ethanol/tertiary-butanol ratio (v/v) is between about 5:1 to 20:1. In some embodiments, the ethanol/tertiary-butanol ratio (v/v) is about 9:1

In one embodiment, the amount of the lipophilic prodrug of mitomycin C in the composition is greater than 5% but less than 30%, such as greater than 5% but less than 20%, by moles of the total moles of the vesicle-forming lipid, lipophilic prodrug of mitomycin C, and optional lipid component. In some embodiments, the amount of the lipophilic prodrug of mitomycin C is about 8, 9, 10, 11 or 12% by moles of the total moles of the vesicle-forming lipid, lipophilic prodrug of mitomycin C, and optional lipid component.

In still another embodiment, the optional lipid component is selected from cholesterol and a conjugate of polyethyleneglycol attached to a lipophilic moiety.

In one embodiment, the amount of the lipophilic prodrug of mitomycin C is greater than 5% but less than 30% by moles of the total moles of the lipids. In some embodiments, the amount of the lipophilic prodrug of mitomycin C is about 10% by moles of the total moles of the liposomes In one embodiment, the ethanol/tertiary-butanol ratio (v/v) is between about 5:1 to 20:1 or is between about 7:1 to 15:1. In one embodiment, the ethanol/tertiary-butanol ratio (v/v) is about 9:1.

In one embodiment, the second fraction is less than about 5% of the population of lipid nanoparticles.

In one embodiment, the second fraction is between about 0.1-5% of the population of lipid nanoparticles In one embodiment, the lipophilic prodrug conjugate of mitomycin C is para-distearoyl-DTB-mitomycin C.

In one embodiment, the vesicle-forming liposome is HSPC.

In one embodiment, the optional lipid component comprises mPEG2000-DSPE.

In one embodiment, the optional lipid component comprises cholesterol and mPEG2000-DSPE.

In one embodiment, the liposomes comprise HSCP, cholesterol, mPEG2000-DSPE, and para-distearoyl-DTB-mitomycin C with HSCP/cholesterol/mPEG2000-DSPE/para-distearoyl-DTB-mitomycin C present at a molar ratio of 55/30/5/10.

In one embodiment, administering the liposomes to a patient in need thereof comprises administering the liposomes in combination with a (second) chemotherapeutic agent. The second chemotherapeutic agent is not a liposomal mitomycin C prodrug or mitomycin C or a non-liposomal mitomycin C prodrug. The chemotherapeutic agents contemplated for use in conjunction with the liposomal mitomycin C prodrug are not limited to any particular compounds or class of compounds. Based on the studies discussed herein below it has been discovered that liposomal-mitomycin C prodrug administered in combination with certain chemotherapeutic agents yields a synergistic effect.

In one embodiment, the chemotherapeutic agent administered in combination with liposomal-mitomycin C prodrug is gemcitabine. Gemcitabine is the generic name assigned to 2'-deoxy-2',2'-difluoro-cytidine. It is commercially available as the monohydrochloride salt, and as the .beta.-isomer. It is also known chemically as 1-(4-amino-2-oxo-1H-pyrimidin-1-yl)-2-desoxy-2,2-difluororibose. Gemcitabine is disclosed in U.S. Pat. Nos. 4,808,614 and 5,464,826, which are incorporated herein by reference for their teaching of how to synthesize, formulate, and use gemcitabine for treating susceptible neoplasms. The commercial formulation of gemcitabine hydrochloride is indicated as first-line treatment for patients with locally advanced (nonresectable Stage II or Stage III) or metastatic (Stage IV) adenocarcinoma of the pancreas, and, in combination with cisplatin or carboplatin, in patients with Non-small cell lung cancer and bladder cancer.

In another embodiment, the chemotherapeutic agent administered in combination with liposomal-mitomycin C prodrug is a vinca alkaloid, such as vinblastine, vinorelbine, vincristine, or vindesine.

In another embodiment, the chemotherapeutic agent administered in combination with liposomal-mitomycin C prodrug is an anthracycline antibiotic, such as doxorubicin or daunorubicin. These anthracycline drugs are widely used in human cancer chemotherapy. And cause DNA damage such as fragmentation and single-strand breaks. The mechanism of action of anthracyclines involves the inhibition of RNA and DNA syntheses. In one embodiment, the doxorubicin or daunorubicin are provided in liposome-entrapped form. pegylated Liposome-entrapped doxorubicin is known by the trade names of DOXIL®, CAELYX®, and LIPO-DOX®, and liposome-entrapped daunorubicin is known by the trade name DAUNOXOME®.

In another embodiment, the chemotherapeutic agent administered in combination with liposomal-mitomycin C prodrug is a taxane. Taxanes are diterpenes produced by the plants of the genus *Taxus* (yews), and are widely used as chemotherapy agents. Taxane agents include paclitaxel (TAXOL®) and docetaxel (TAXOTERE®).

In another embodiment, the chemotherapeutic agent administered in combination with liposomal mitomycin C prodrug is a fluoropyrimidine. Fluoropyrimidines are antimetabolite drugs widely used in the treatment of cancer including colorectal and breast cancer and cancers of the aerodigestive tract. The fluoropyrimidines include the drugs 5-fluorouracil (5-FU) and prodrugs of 5-FU, such as capecitabine and tegafur. In one embodiment, the fluoropyrimidine chemotherapeutic agent administered in combination with liposomal mitomycin C prodrug is a prodrug for 5-FU, such as capecitabine. Capecitabine is a fluoropyrimidine carbamate with antineoplastic activity. It is an orally administered systemic prodrug of 5'-deoxy-5-fluorouridine (5'-DFUR) which is converted to 5-fluorouracil. The chemical name for capecitabine is 5'-deoxy-5-fluoro-N-[(pentyloxy)carbonyl]-cytidine. It is marketed in the United States as XELODA® (Roche Laboratories). It is indicated for the treatment of patients with metastatic breast cancer and colorectal tumors by oral route. Capecitabine is described in U.S. Pat. No. 5,472,949.

Methods for the safe and effective administration of these chemotherapeutic agents are known to those skilled in the art. In addition, their administration is described in the standard literature. For example, the administration of many of the chemotherapeutic agents is described in the "Physicians' Desk Reference" (PDR), e.g., 1996 edition (Medical Economics Company, Montvale, N.J.).

When a liposomal-mitomycin C prodrug is administered in combination with at least one other agent, the at least one other agent can be co-administered in the same formulation. Alternatively, the various agents can be administered simultaneously (concurrently) in separate formulations. In addition, the agents can be administered in separate formulations, where the separate formulations are not administered simultaneously but are administered sequentially immediately with little or no time lapse between administration, or are administered sequentially during the same period of treatment, for example, during a daily or weekly period of treatment.

Accordingly, in the method of the present invention, administration of liposomal-mitomycin C prodrug "in combination with" a second chemotherapeutic agent refers to co-administration, which can intend administration concurrently, sequentially, or alternately. Concurrent administration refers to administration of both the liposomal-mitomycin C prodrug and the second chemotherapeutic agent at essentially the same time. Concurrent administration can be achieved via a single, combined formulation, containing both an amount of liposomal-mitomycin C prodrug that yields an effective amount of mitomycin C and an amount of the second chemotherapeutic agent in physical association with one another. The single, combined formulation may consist of a liquid mixture containing amounts of both liposomal-mitomycin C prodrug and second chemotherapeutic agent, which may be injected into the subject. It is also within the confines of the present methods that an amount of liposomal-mitomycin C prodrug and an amount of second chemotherapeutic agent be administered concurrently to a subject from separate, individual formulations. For example, the liposomal-mitomycin C prodrug can be administered via injection and the amount of second chemotherapeutic agent can be administered orally or via a different or same route of injection than that used for injection of the liposomal-mitomycin C prodrug.

In the methods described herein, liposomal-mitomycin C prodrug and the second chemotherapeutic agent also may be co-administered to a subject from separate, individual formulations that are spaced out over a period of time, so as to obtain the maximum efficacy of the combination. Administration of each drug may range in duration from a brief, rapid administration to a continuous perfusion. When spaced out over a period of time, co-administration of liposomal-mitomycin C prodrug and the second chemotherapeutic agent may be sequential or alternate. For sequential co-administration, one of the agents is separately administered, followed by the other. For example, a full course of treatment with liposomal-mitomycin C prodrug may be completed, and then may be followed by a full course of treatment with the second chemotherapeutic agent. Alternatively, for sequential co-administration, a full course of treatment with the second chemotherapeutic agent may be completed, then followed by a full course of treatment with liposomal-mitomycin C prodrug. For alternate co-administration, partial courses of treatment with liposomal-mitomycin C prodrug may be alternated with partial courses of treatment with the second chemotherapeutic agent, until a full treatment of each drug has been administered.

In one embodiment, administering the liposomes to a patient in need thereof comprises administering the liposomes in combination with radiation therapy. Radiation therapy uses high-energy radiation to damage and/or kill cancer cells and to shrink tumors. The high-energy radiation may involve x-rays, gamma rays or charged particles. The radiation therapy may be delivered by a machine positioned outside the body (external-beam radiation therapy), or it may come from radioactive material placed in the body near cancer cells (internal radiation therapy, also called brachytherapy). Systemic radiation therapy uses radioactive substances, such as radioactive iodine, that travel in the blood to kill cancer cells.

Accordingly, in one embodiment, radiotherapy intends external radiotherapy where the radiation comes from an instrument outside the body. External radiotherapy is usually given as a course of several treatments over days or weeks and during a treatment a machine directs the high-energy radiation, usually X-rays, at the cancer site and a small area of normal tissue surrounding it.

In another embodiment, radiotherapy intends internal radiotherapy where the radiation comes from an implant or a material (liquid, solid, semi-solid or other substance) placed inside the body. In one embodiment, the internal radiotherapy is brachytherapy where a solid radioactive source is placed inside a body cavity or needles are placed in the tumor. In another embodiment, the internal radiotherapy comprises administering a liquid source of radiation, typically a radionuclide (radioisotope or unsealed source). The radiation source may be orally administered or may be injected into a vein.

IV. Exemplary Studies

In a first study, prodrug conjugate of mitomycin C was incorporated into a liposome delivery platform as described in Example 1. The liposomes were prepared by a process comprising dissolving HSCP/cholesterol/mPEG2000-DSPE/para-distearoyl-DTB-mitomycin C in a solvent mixture with different ratio (v/v) of ethanol/tertiary-butanol. The liposome samples were imaged using cryo-TEM. Unless otherwise indicated, HSCP/cholesterol/mPEG2000-DSPE/para-distearoyl-DTB-mitomycin C were present at a molar ratio of 55/30/5/10 (75.5 mg/ml lipid and 12.5 mg/ml prodrug).

Figure 1B:
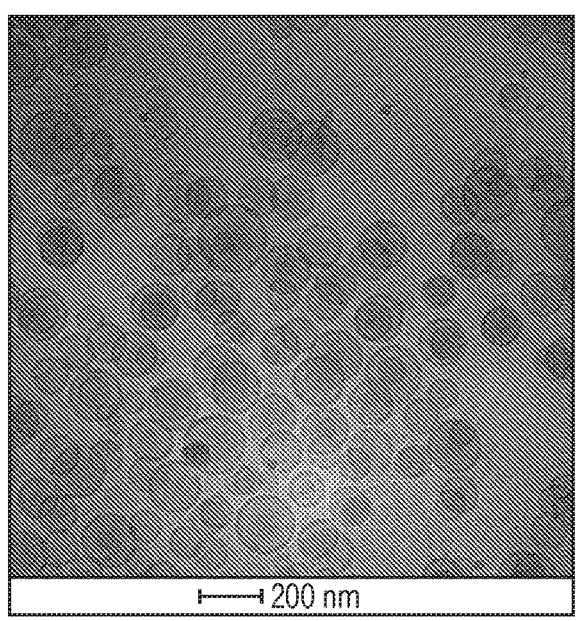
Figure 1C:
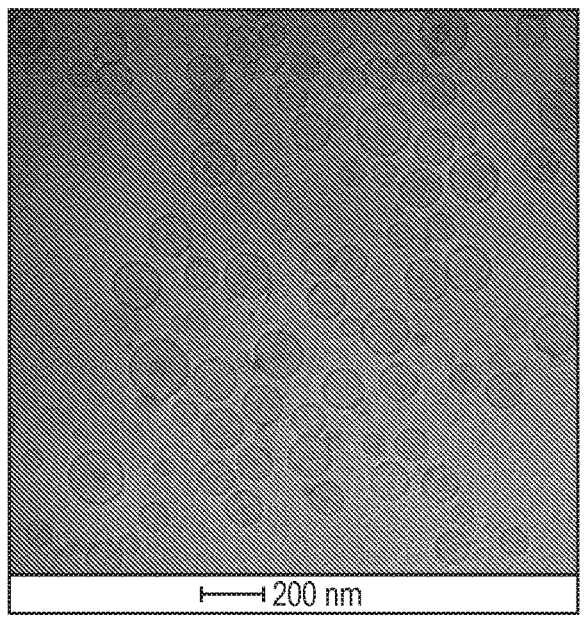
Figure 1D:
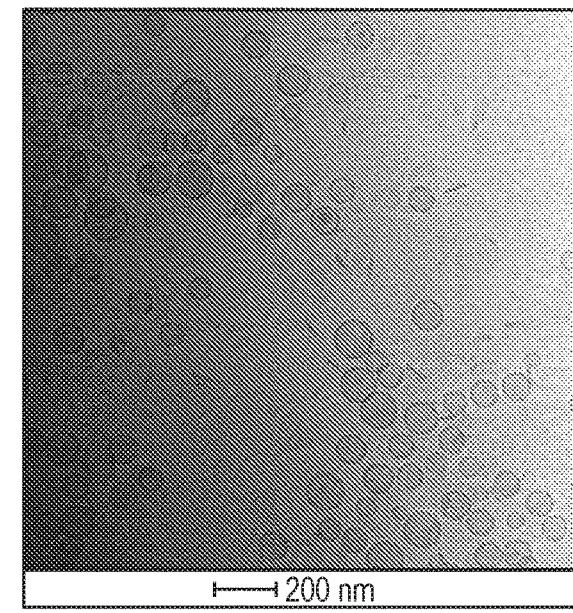

FIGS. 1A-1D are cryo-TEM images of liposomes which were prepared by a process comprising dissolving HSPC/cholesterol/mPEG2000-DSPE/para-distearoyl-DTB-mitomycin C in a solvent with ratio (v/v) of ethanol/tertiary-butanol as 50:50 (FIG. 1D), 75:25 (FIG. 1C), 90:10 (FIG. 1A), or 100:0 (FIG. 1B). Cryo-TEM image analysis showed that the higher the content of tertiary-butanol is, the more the rod-shaped particles formed. When tertiary butanol was 50% in the solvent mixture, more rod-shaped particles formed than when tertiary butanol was 25%. When tertiary butanol was 10% in the solvent mixture, practically no rods were detected.

Figure 2A:
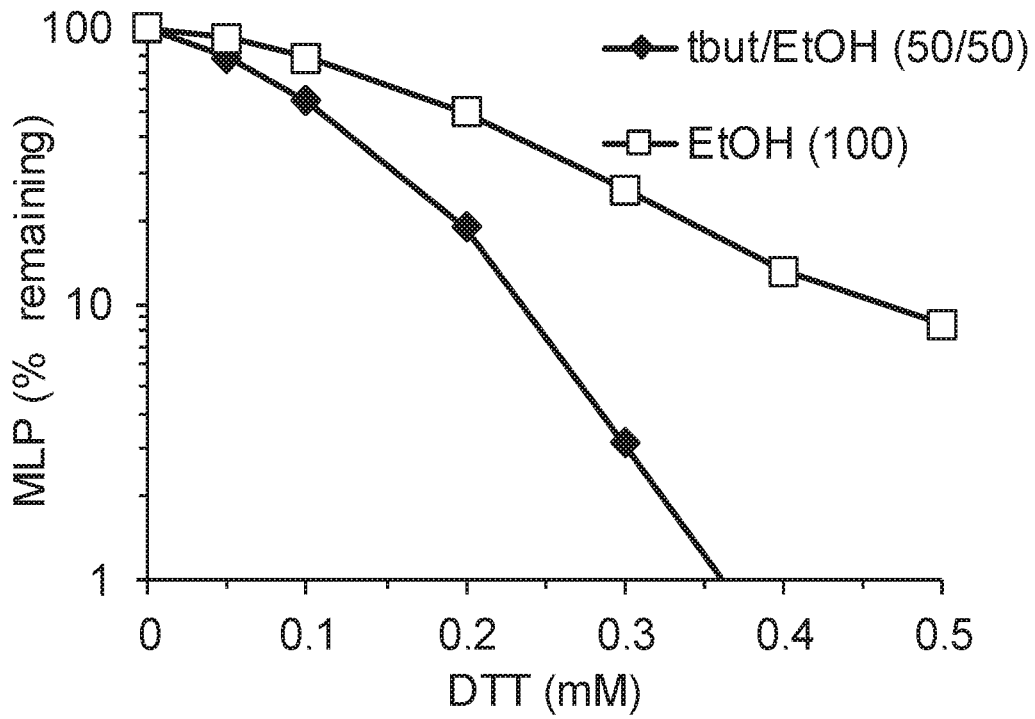
FIG. 2A is a graph showing in-vitro dithiothreitol (DTT) cleavage of liposomal prodrug prepared from by a process comprising dissolving liposome components in a solvent with a ratio (v/v) of ethanol/tertiary-butanol at 50:50 or in ethanol
Figure 2B:
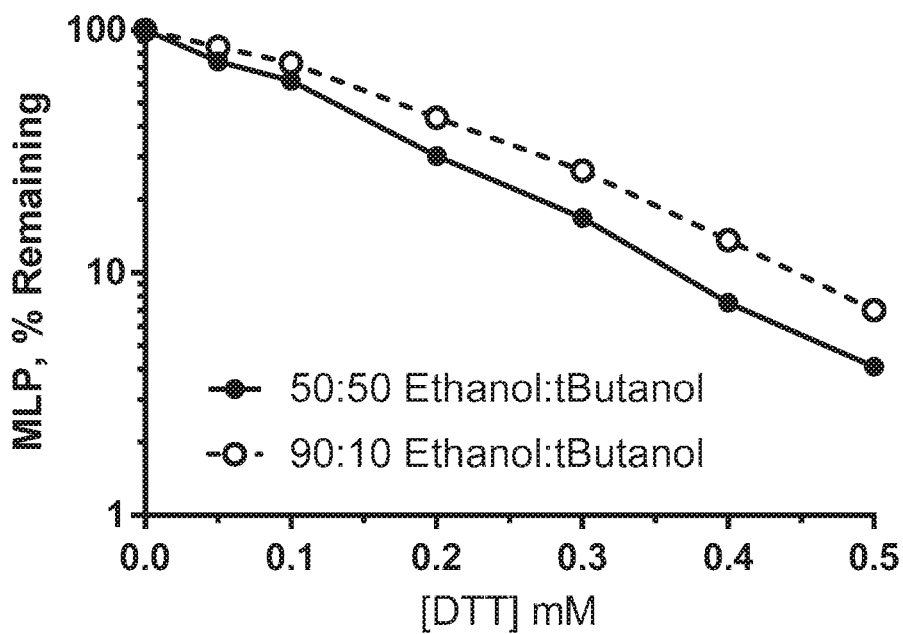
FIG. 2B is a graph showing in-vitro dithiothreitol (DTT) cleavage of liposomal mitomycin C prodrug prepared from by a process comprising dissolving liposome components in a solvent with a ratio (v/v) of ethanol/tertiary-butanol at 50:50 or 90:10.

In another study, an in vitro DTT-induced release/activation assay was performed on liposomal prodrug conjugate of mitomycin C. FIGS. 2A-2B show that the liposomes prepared by a process comprising dissolving HSPC/cholesterol/mPEG2000-DSPE/para-distearoyl-DTB-mitomycin C in a solvent with ratio (v/v) of ethanol/tertiary-butanol as 50:50 were more sensitive to DTT-induced cleavage than liposomes prepared by a process comprising dissolving HSPC/cholesterol/mPEG2000-DSPE/para-distearoyl-DTB-mitomycin C in 100% (FIG. 2A) or 90% ethanol (FIG. 2B).

Figure 3A:
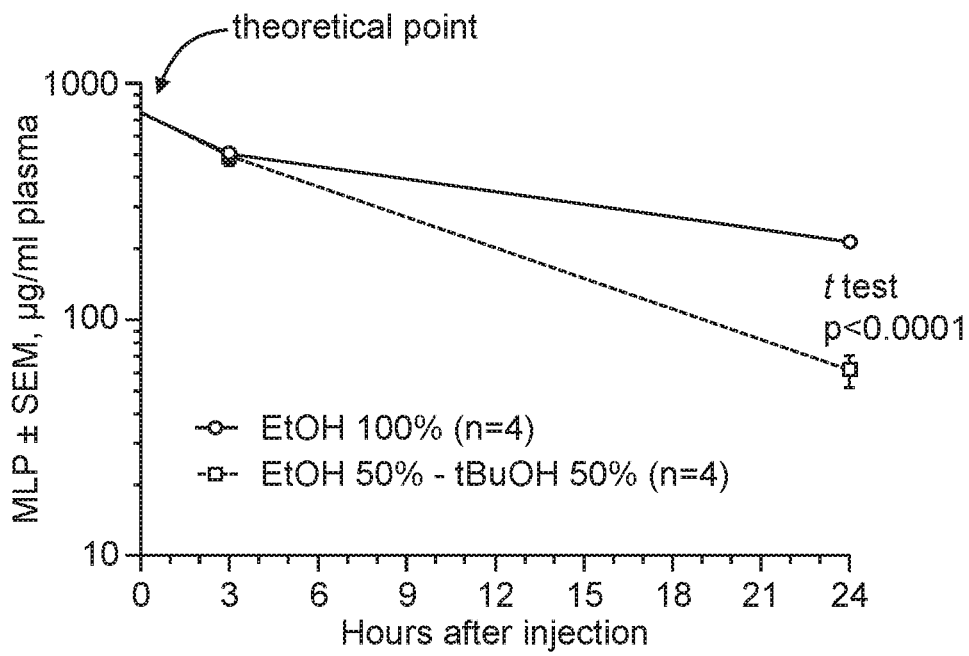
FIGS. 3A-3C are graphs showing the plasma level, in μg/mL, of a mitomycin C prodrug in mice as a function of time, in hours, after intravenous administration of liposomes prepared by a process comprising dissolving liposome components in a solvent with ratio (v/v) of ethanol/tertiary-butanol as 50:50 90:10, or 100:0.
Figure 3B:
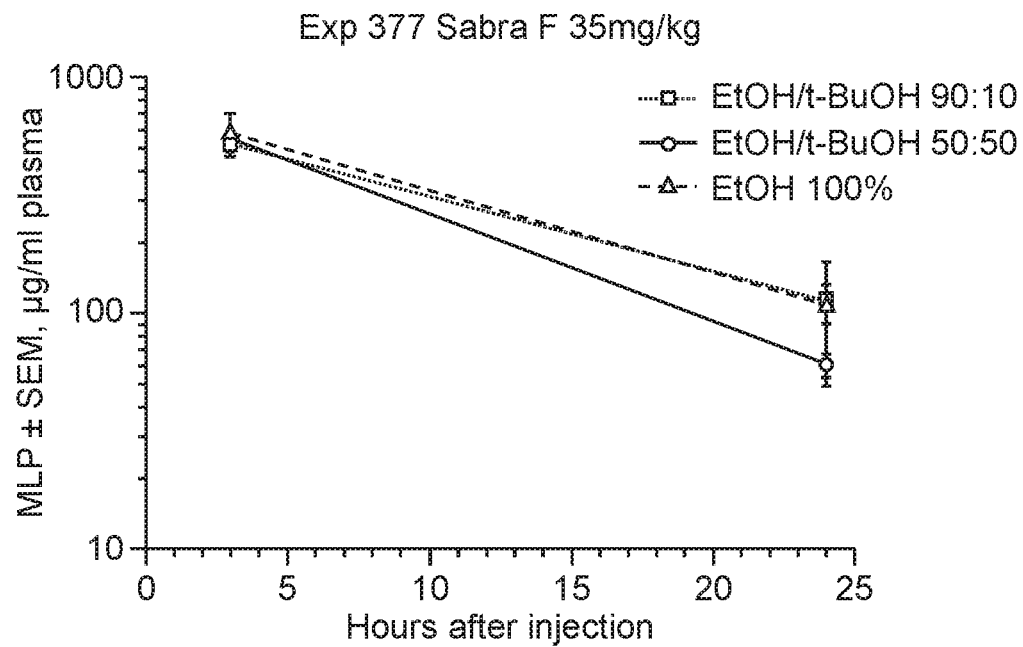
Figure 3C:
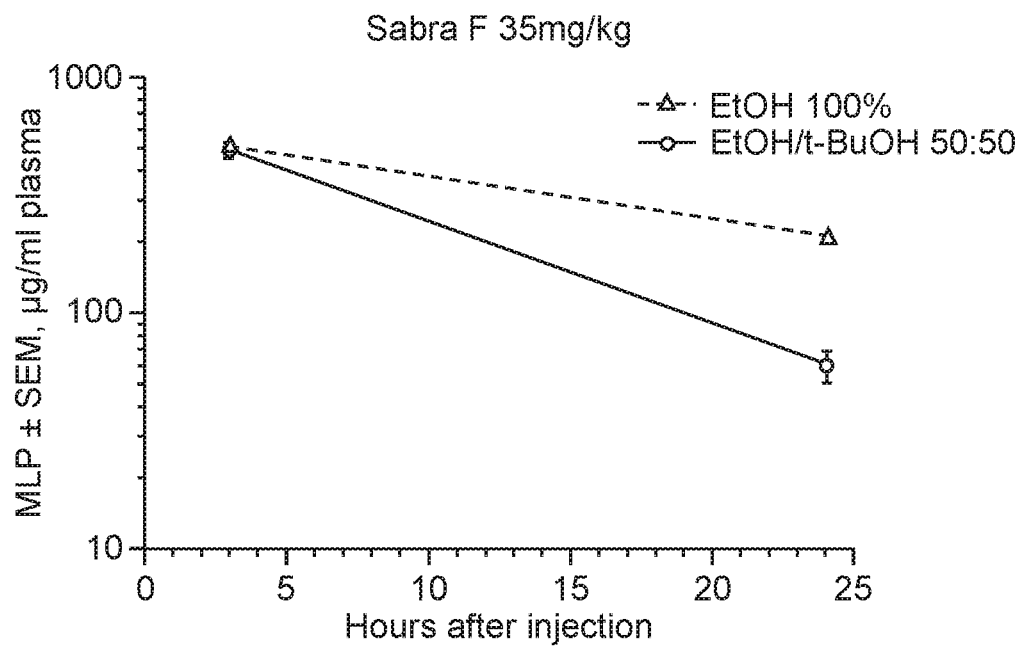

In another study, a pharmacokinetic study on mice was conducted. This study aimed to measure the plasma level of para-distearoyl-DTB-mitomycin C by administering intravenously to mice liposomes prepared by a process comprising dissolving HSPC/cholesterol/mPEG2000-DSPE/para-distearoyl-DTB-mitomycin C in a solvent with ratio (v/v) of ethanol/tertiary-butanol as 50:50, 90:10, or 100:0. FIGS. 3A-3C show that plasma levels of the mitomycin C prodrug were comparable at 3 hours after injection, but at 24 hours a gap (>3-fold) opens in favor of the batches prepared from using low content of tertiary butanol, indicating a higher plasma level and longer time of circulation of the mitomycin C prodrug delivered by liposomes prepared from using low or no content of tertiary butanol.

Figure 4:
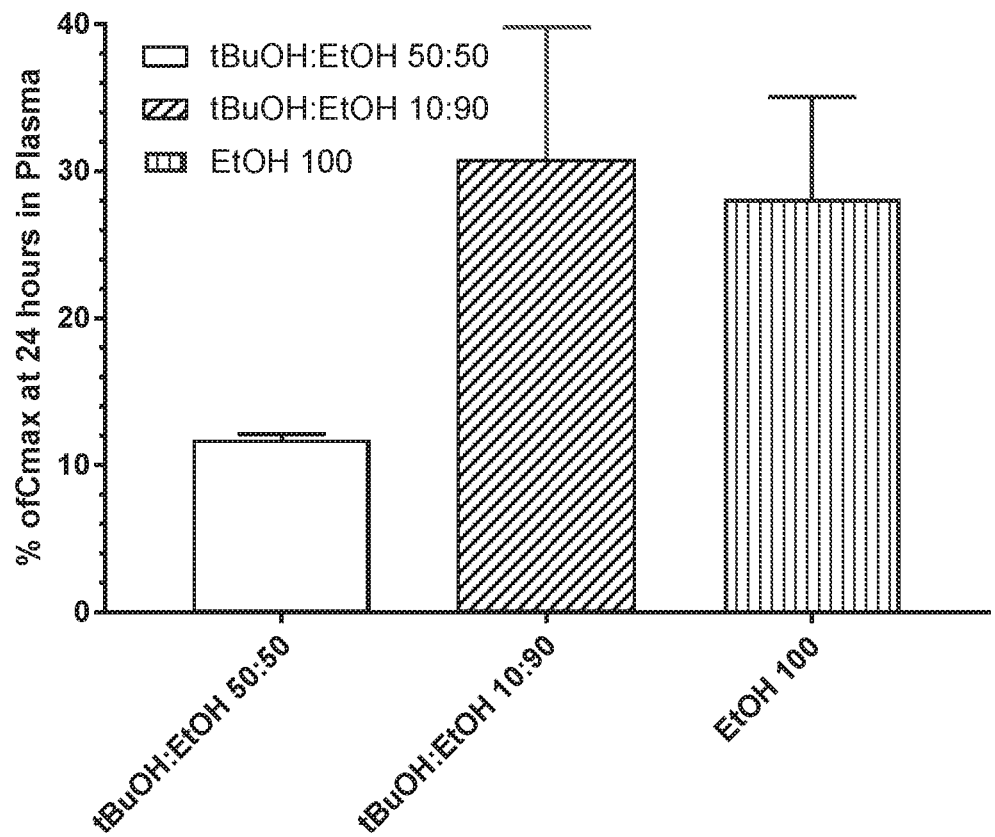
FIG. 4 is a bar graph showing the plasma level of a liposomal mitomycin C prodrug in mice as a percentage of Cmax at 24 hours after intravenous administration of liposomes prepared by a process comprising dissolving a vesicle-forming lipid and the prodrug of mitomycin C in a solvent with ratio (v/v) of ethanol/tertiary-butanol as 50:50, 90:10, or 100:0.

FIG. 4 is a bar graph showing the mice plasma level of the liposomal mitomycin C (MLP) prodrug at 24 hours after intravenous administration as a percentage of Cmax (Cmax is normally achieved within the $1^{st}$ hour after intravenous injection of a liposome formulation comprising MLP) after intravenous administration to the mice of liposomes prepared by a process comprising dissolving HSPC/cholesterol/mPEG2000-DSPE/para-distearoyl-DTB-mitomycin C in a solvent with ratio (v/v) of ethanol/tertiary-butanol as 50:50, 90:10, or 100:0. The liposomes prepared from a solvent with ratio (v/v) of ethanol/tertiary-butanol as 90:10 has the highest percentage of Cmax at 24 hours.

Figure 5A:
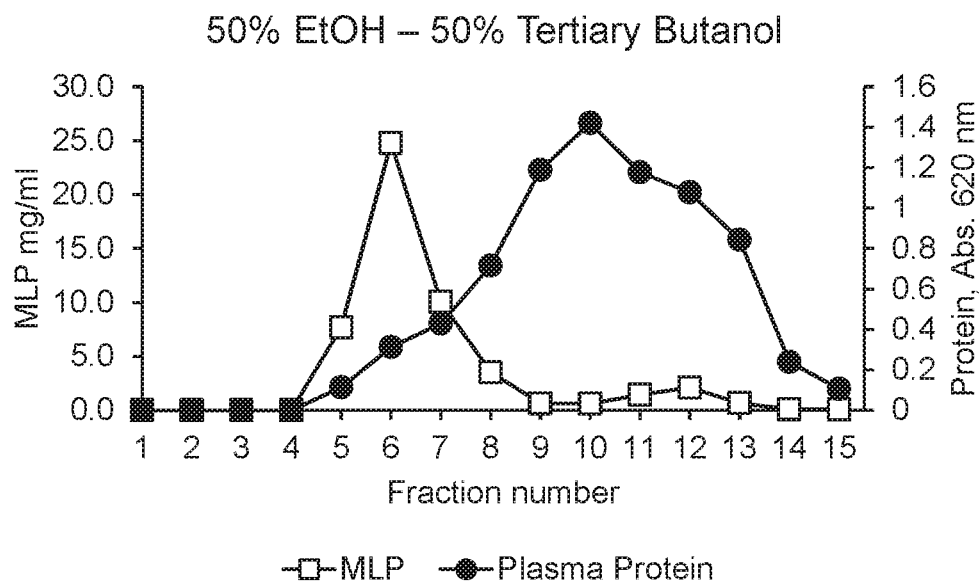
FIGS. 5A and 5B is a graph showing in vitro plasma stability of a liposomal mitomycin C prodrug prepared by a process comprising dissolving liposome components in a solvent with ratio (v/v) of ethanol/tertiary-butanol as 50:50 (FIG. 5A) or 90:10 (FIG. 5B).
Figure 5B:
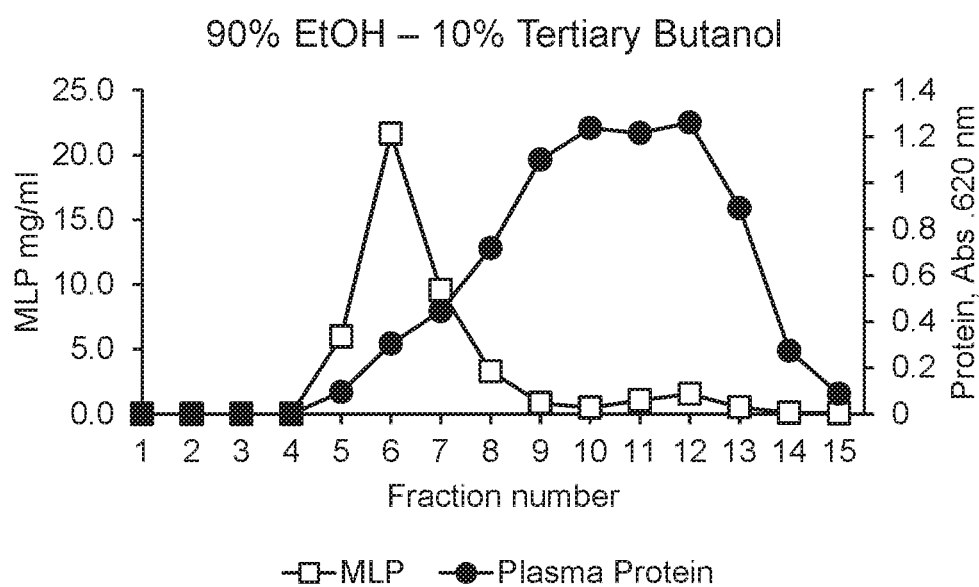

FIGS. 5A and 5B are graphs showing in vitro plasma stability of a formulation of liposomal mitomycin C prodrug prepared by a process comprising dissolving liposome components in a solvent with ratio (v/v) of ethanol/tertiary-butanol as 50:50 (FIG. 5A) or 90:10 (FIG. 5B). This in vitro plasma stability assay shows no difference between tBuOH-high and tBuOH-low, indicating that the presence of rod-shaped lipid nanoparticles does not affect the plasma stability of the liposomal mitomycin C prodrug.

Figure 6:
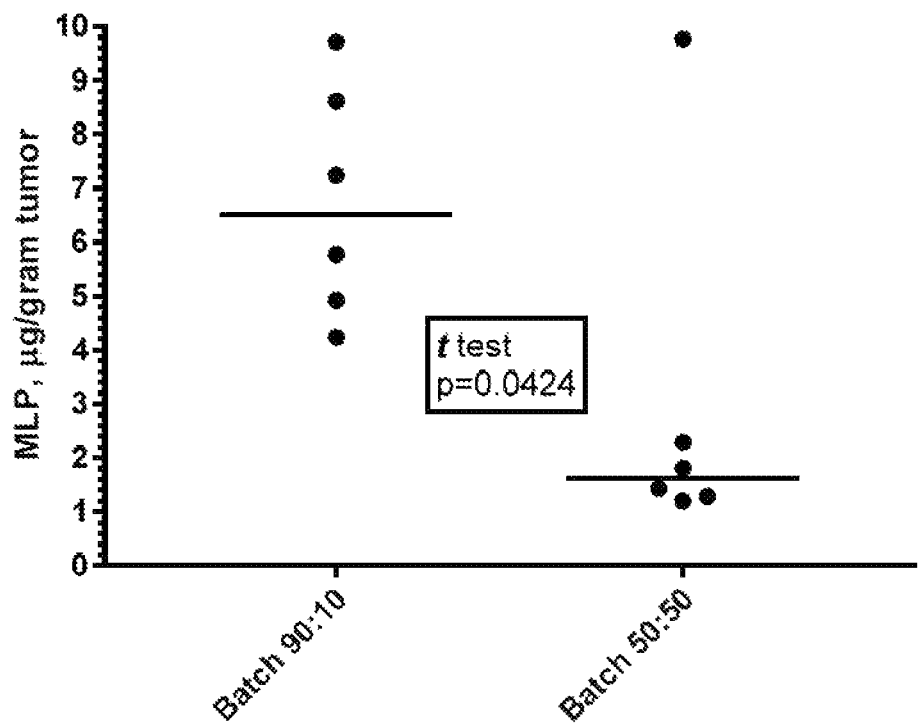
FIG. 6 is a graph showing the concentration of liposomal mitomycin C prodrug (MLP) in each tumor (μg of MLP/g of tumor) at the time point of 24 hours after IV injection of liposomal mitomycin C prodrug prepared by a process comprising dissolving liposome components in a solvent with ratio (v/v) of ethanol/tertiary-butanol as 90/10 or 50/50.

FIG. 6 shows the concentration of liposomal mitomycin C prodrug (MLP) in each tumor (μg of MLP/g of tumor) at the time point of 24 hours after IV injection of liposomal mitomycin C prodrug prepared by a process comprising dissolving liposome components in a solvent with ratio (v/v) of ethanol/tertiary-butanol as 90/10 or 50/50. The ratio of ethanol/t-butanol (v/v) used to prepare liposomal mitomycin C prodrug can affect the uptake of the liposomal mitomycin C prodrug into the tumors. 24 hours after IV injection of liposomal mitomycin C prodrug prepared by using a solvent with ratio (v/v) of ethanol/tertiary-butanol as 90/10 or 50/50, the concentration of liposomal mitomycin C prodrug in tumor is statistically significantly higher for liposomal mitomycin C prodrug prepared by using the solvent with ratio (v/v) of ethanol/tertiary-butanol as 90/10. For the liposomes prepared with a 50:50 ratio of ethanol/tertiary-butanol, the median concentration of MLP was 1.63 μg/g tumor, with a range of 1.20-9.76 μg/g tumor. For the liposomes prepared with a 90:10 ratio of ethanol/tertiary-butanol, the median concentration of MLP was 6.51 μg/g tumor, with a range of 4.23-9.71 μg/g tumor. Thus, there was a higher concentration of MLP in the tumor after administration of a liposome composition with a reduced population of rod-shaped lipid nanoparticles.

Another study was conducted to demonstrate that rod-shaped liposomes contribute to high sensitivity to cleavage in vitro and fast clearance in vivo. In this study, two compositions with liposomal mitomycin C prodrug (MLP) were prepared. The two compositions were prepared identically except one composition had 20% PEG-lipid rather than 5% PEG-lipid. Increasing the amount of PEG-lipid promotes formation of micellar disks and rods (Sandstrom, M. C. et al., *Langmuir*, 23(8):4192 (2007); Zhang, W. et al., *European Journal of Pharmaceutical Sciences*, 125:74-85 (2018)). TEM inspection of the two compositions confirmed the composition with 25% PEG-lipid was rich in rod-shaped liposomes. The two compositions were tested in vitro using the release assay described in Example 2. The composition with a substantial fraction of rod-shaped liposomes (i.e., the composition with 25% PEG-lipid) was more sensitive to cleavage with dithiothreitol. The two compositions were tested in vivo to evaluate plasma clearance, according to the methods of Example 3. The composition with a substantial fraction of rod-shaped liposomes (i.e., the composition with 25% PEG-lipid) was cleared from circulation more rapidly than the liposomes prepared to the methods described herein to have a small fraction (e.g., less than about 15%) of rod-shaped liposomes.

V. Examples

The following examples are illustrative in nature and are in no way intended to be limiting.

Example 1

Liposomal Mitomycin C Prodrug Preparation

A prodrug conjugate of mitomycin C releasably attached to a lipophilic moiety, para-diacyldiglyceroldithiobenzal-mitomycin C, was synthesized as described in U.S. Pat. No. 6,365,179, in Example 2, incorporated by reference herein.

A mixture of HSPC, cholesterol, mPEG2000-DSPE, and para-diacyldiglycerolditiobenzyl-mitomycin C at a molar ratio 55:30:5:10, respectively, was dissolved in ethanol/tertiary butanol (50:50, 75:25, 90:10, or 100:0) and mixed with 5% dextrose/sodium phosphate buffer 20 mM, pH 7.0 at a 20:80 v/v ratio. The liposome suspension was extruded under high pressure through stacked polycarbonate membranes of 0.08 or 0.10 μm pore size at 65° C. Organic solvents were removed by dialysis, or diafiltration against the buffer. The liposome formulation was adjusted to a final prodrug concentration of 5 mg/mL and sterile-filtered through 0.22 μm membranes.

The images of the liposomes were obtained using cryo-TEM. (FIG. 1B) are cryo-TEM images of liposomes prepared from using a solvent with ratio (v/v) of ethanol/tertiary-butanol as 50:50 (FIG. 1D), 75:25 (FIG. 1C), 90:10 (FIG. 1A), or 100:0 (FIG. 1B).

Example 2

DTT-Induced Cleavage of Mitomycin C from the Liposomes

The release of active mitomycin C (MMC) from the liposomal formulation occurs through reduction of the MLP (liposomal prodrug of mitomycin C). It was examined in batches of MLP (prepared using EtOH 100%, 90% or 50%) by treatment with dithiothreitol (DTT), a potent reducing agent, and determination of the remaining amount of MLP and released free mitomycin C.

An assay for demonstrating release of MMC from MLP by incubation with DTT was developed to verify consistent drug release from prodrug. 500 μg of MLP (0.1 ml) was incubated with various concentrations of DTT at 37° C. for 1 h with shaking. The reaction was stopped by dilution and drug extraction with Isopropanol (1:10). MLP and MMC were quantified by HPLC. Following drug extraction, the supernatants were filtered and run on a LaChrom Merck Hitachi HPLC system with a Phenomenex Hypersil BDS C18 column; 130 A 150×4.60 mm 5 μm, in a mobile phase composed of methanol:isopropanol 70/30, at a flow rate of 1 ml/min, with UV detection at 360 nm. MLP retention time under these conditions was 5.5 min. MMC retention time was close to the front at 1.5 min. Peak areas were quantified and compared to standard curves of MLP.

FIGS. 2A and 2B show the DTT-induced cleavage of mitomycin c from the liposomes prepared from using a solvent with ratio (v/v) of ethanol/tertiary-butanol as 50:50, 90:10, and 100:0.

Example 3

In Vivo Pharmacokinetic Study

The pharmacokinetics of MLP liposomes prepared from using a solvent with ratio (v/v) of ethanol/tertiary-butanol as 50:50, 90:10, or 100:0 was tested. Groups of 3-4 Sabra mice (FIGS. 3A-3C) or BalbC mice (FIG. 4) were injected IV with 35 mg/kg liposomal MLP of each of these batches. Three hours or 24 hours after liposome injection, mice were anesthetized with isoflurane, bled from the retro-orbital venous sinuses into heparin containing tubes, and then sacrificed. Plasma was isolated by centrifugation at 3000 rpm for 15 min and extracted 1:10 in IPA, followed by centrifugation to remove proteins. The supernatant was analyzed for MLP content by HPLC as described above.

FIGS. 3A-3D show the plasma levels of the mitomycin C prodrug in mice as a function of time after intravenous administration of liposomes prepared from using a solvent with ratio (v/v) of ethanol/tertiary-butanol as 50:50, 90:10, or 100:0.

FIG. 4 shows the mice plasma level of the mitomycin C prodrug as a percentage of Cmax at 24 hours after intravenous administration to the mice of liposomes prepared from using a solvent with ratio (v/v) of ethanol/tertiary-butanol as 50:50, 90:10, or 100:0.

Example 4

In Vitro Plasma Stability

Incubation of the batch prepared with ethanol/t-butanol (90/10, v/v) did not affect the plasma stability profile of liposomal mitomycin C prodrug ("MLP"). HPLC determination of MLP confirms that in both batches it remains about 100% intact during exposure to 80% human plasma for 24 h at 37° C. Gel chromatography elution profile of both batches of MLP incubated at 37° C. for 24 h in plasma. Liposomes elute in fractions 5-7; plasma proteins elute mostly in fractions 8-13. No significant leakage of MLP to protein and low molecular weight fractions was seen with any of the formulations. See FIG. 5A and FIG. 5B.

Example 5

In Vivo Uptake of Liposomal Mitomycin C Prodrug in Tumor

Two formulations of MLP-comprising liposomes were prepared by dissolving lipids (HSPC and MLP (HSPC:cholesterol:mPEG-DSPE:MLP, molar ratio 55:30:510) in a solvent mixture of either ethanol/tertiary-butanol 50:50 v/v ratio or ethanol/tertiary-butanol 90:10 v/v ratio. These formulations were then processed to generate liposome suspensions with MLP at a concentration of 5 mg/mL.

BALB/c female mice aged 8-10 weeks, were inoculated subcutaneously with M109 tumor cells (1 million cells per mouse). Twenty days following tumor inoculation, mice bearing palpable tumors were divided in two groups and each group was injected IV with 30 mg/kg liposomal MLP of a liposome composition (ethanol/tertiary-butanol 50:50 and ethanol/tertiary-butanol 90:10). 24 hours after liposome injection, mice were sacrificed. For tissue extraction of MLP, tissue samples (including tumors) weighing approximately 140-200 mg were homogenized in 0.5 mL (final volume) of isopropanol and centrifuged at 3000 rpm for 15 minutes. Supernatants were filtered and run on HPLC system to determine the concentration of MLP in each tumor (μg of MLP/g of tumor). Results are shown in FIG. 6.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

It is claimed:

1. A composition comprising:
a population of lipid nanoparticles and a pharmaceutically acceptable vehicle,
wherein the population of lipid nanoparticles is comprised of spherical liposomes and rod-shaped lipid nanoparticles, where less than about 5% of the population of lipid nanoparticles is rod-shaped lipid nanoparticles and, wherein the spherical liposomes are comprised of a vesicle-forming lipid, a lipophilic prodrug of mitomycin C, and an optional lipid component.

2. The composition of claim 1, wherein the amount of the lipophilic prodrug of mitomycin C is between about 8-12% by moles of the total moles of the vesicle-forming lipid, lipophilic prodrug of mitomycin C, and optional lipid component.

3. The composition of claim 1, wherein the rod-shaped lipid nanoparticles comprise between about 0.1% and less than about 5% of the population of lipid nanoparticles.

4. The composition of claim 1, wherein the population of lipid nanoparticles is manufactured by a process comprising dissolving the vesicle-forming lipid, lipophilic prodrug of mitomycin C, and optional lipid component in a solvent mixture comprised of ethanol and tertiary butanol in an ethanol/tertiary-butanol ratio (v/v) of between about 2:1 to 20:1.

5. The composition of claim 4, wherein the ethanol/tertiary-butanol ratio (v/v) is between about 5:1 to 20:1.

6. The composition of claim 5, wherein the ethanol/tertiary-butanol ratio (v/v) is about 9:1.

7. The composition of claim 1, wherein the liposomal prodrug of mitomycin C of the composition has an IV blood circulation half-life in mice of at least about 15 hours.

8. The composition of claim 1, wherein, comparing to liposomal prodrug of mitomycin C of a composition comprising equal to or greater than 15% of rod-shaped lipid nanoparticles, the liposomal prodrug of mitomycin C of the composition has an IV blood circulation half-life in mice that is closer in value to the IV blood circulation half-life in mice of pegylated liposomal doxorubicin.

9. The composition of claim 1, wherein the rod-shaped lipid nanoparticles in the population of lipid nanoparticles are present in a number that is less than the number of rod-shaped lipid nanoparticles in a liposome composition prepared from a 50:50 ethanol/tertiary-butanol solvent mixture.

10. A method for the manufacture of liposomes, comprising:
dissolving a vesicle-forming lipid, a lipophilic prodrug of mitomycin C, and an optional lipid component in a solvent mixture comprised of ethanol and tertiary butanol in an ethanol/tertiary-butanol ratio (v/v) of between about 2:1 to 20:1 to form a dissolved lipid solution, and
forming a population of lipid nanoparticles, wherein the population of lipid nanoparticles is comprised of spherical liposomes and rod-shaped lipid nanoparticles, where less than about 5% of the population of lipid nanoparticles are rod-shaped lipid nanoparticles.

11. The method of claim 10, wherein forming the population of lipid nanoparticles comprises mixing the dissolved lipid solution with an aqueous buffer to form a suspension, extruding the suspension through filters, and removing the mixture of ethanol and tertiary-butanol.

12. The method of claim 11, wherein forming the population of lipid nanoparticles further comprises sterile filtration.

13. The method of claim 10, wherein the amount of the lipophilic prodrug of mitomycin C is between about 8-12% by moles of the total moles of the vesicle-forming lipid, lipophilic prodrug of mitomycin C, and optional lipid component.

14. The method of claim 10, wherein the ethanol/tertiary-butanol ratio (v/v) is between about 5:1 to 20:1.

15. The method of claim 14, wherein the ethanol/tertiary-butanol ratio (v/v) is between about 7:1 to 15:1.

16. The method of claim 15, wherein the ethanol/tertiary-butanol ratio (v/v) is about 9:1.

17. The method of claim 10, wherein the second fraction is less than about 5% of the population of lipid nanoparticles.

18. A population of lipid nanoparticles prepared by a process, comprising:
dissolving a vesicle-forming lipid, a lipophilic prodrug of mitomycin C, and an optional lipid component in a solvent mixture comprised of ethanol and tertiary butanol in an ethanol/tertiary-butanol ratio of between about 2:1 to 20:1 to form a dissolved lipid solution; and
mixing the dissolved lipid solution with an aqueous buffer to form a population of lipid nanoparticles, wherein the population of lipid nanoparticles is comprised of spherical liposomes and rod-shaped lipid nanoparticles, where less than about 5% of the population of lipid nanoparticles are rod-shaped lipid nanoparticles.

19. A method for treating cancer, comprising: administering a composition of claim 1 to a patient in need thereof in an amount that provides a therapeutically-effective amount of mitomycin C for the treatment of cancer.

* * * * *